United States Patent [19]

Legerton et al.

[11] Patent Number: 5,662,706
[45] Date of Patent: Sep. 2, 1997

[54] VARIABLE TRANSMISSIVITY ANNULAR MASK LENS FOR THE TREATMENT OF OPTICAL ABERRATIONS

[75] Inventors: Jerome A. Legerton, Los Gatos; Chun-Shen Lee, Cupertino; John M. Evans, Fremont; Praful C. Doshi, Poway, all of Calif.

[73] Assignee: PBH, Inc., Sunnyvale, Calif.

[21] Appl. No.: 663,622

[22] Filed: Jun. 14, 1996

[51] Int. Cl.⁶ .................................................. A61F 2/16
[52] U.S. Cl. ......................... 623/6; 351/160 R; 351/162
[58] Field of Search ........................ 623/6, 5; 351/160 R, 351/161, 162

[56] References Cited

U.S. PATENT DOCUMENTS

| | | | |
|---|---|---|---|
| 3,536,386 | 10/1970 | Spivack | 351/160 R |
| 3,946,982 | 3/1976 | Calkins et al. | 249/102 |
| 4,582,402 | 4/1986 | Knapp | 351/162 |
| 4,702,574 | 10/1987 | Bawa | 351/162 |
| 4,955,904 | 9/1990 | Atebara et al. | 623/6 |
| 4,994,080 | 2/1991 | Shepard | 623/5 |
| 5,089,024 | 2/1992 | Christie et al. | 623/6 |
| 5,108,169 | 4/1992 | Mandell | 351/161 |
| 5,245,367 | 9/1993 | Miller et al. | 351/161 |

FOREIGN PATENT DOCUMENTS

| | | | |
|---|---|---|---|
| 0 225 098 | 6/1987 | European Pat. Off. | |
| 1115140 | 12/1955 | France | |
| 1400566 | 4/1965 | France | |
| 2599-156 | 5/1986 | France | 351/160 R |
| 3-1857 | 1/1991 | Japan | |
| 1276003 | 6/1972 | United Kingdom | |
| WO94/23327 | 10/1994 | WIPO | |

OTHER PUBLICATIONS

Bier, *Prescribing for Presbyopia with Contact Lenses*, The Ophthalmic Optician, 5(9):439–455 (1965).

Contact Lens Practice, pp. 394–398, 644–646, 655–656.

Groppi, *New Aspects in the Fitting of the Multi-Range Bifocal Contact Lens*, Contacto, 15(2):22–29 (1971).

Mazow, *The Pupilens—A Preliminary Report*, International Contact Lens Congress in Munich, Aug. (1958).

Neefe, *Neefe Special Contact Lenses*, Contacto, Nov. (1975).

Rosenbloom, *The Controlled-Pupil Contact Lens in Low Vision Problems*, Journal of the American Optometric Association 40(8):836–840 (1969).

Wesley, *A New Concept in Successful Bifocal Contact Lens Fitting*, pp. 71–73.

Primary Examiner—Mary Beth Jones
Attorney, Agent, or Firm—Burns, Doane, Swecker & Mathis, L.L.P.

[57] ABSTRACT

An annular mask lens for the treatment of optical aberrations such as but not limited to night myopia, spherical aberration, aniridia, keratoconus, corneal scarring, penetrating keratoplasty, and post refractive surgery complication. The lens has an annular mask having an aperture larger than conventional pinhole contact lens. The aperture having a "soft" inside edge and which mask has a gradually increasing transmissivity radially toward the outer edge of the mask.

32 Claims, 5 Drawing Sheets

VARIABLE TRANSMISSIVITY ANNULAR MASK LENS FOR THE TREATMENT OF OPTICAL ABERRATIONS

FIELD OF THE INVENTION

This invention concerns an annular mask lens. The size of the aperture defined by the annular mask of the lens of the present invention function to reduce peripheral aberrations and distortion. The aperture is of a size greater conventional "pinhole" contact lenses which produce refractive correction. The aperture is sized for improving the vision of individuals with night myopia, spherical aberration, aniridia, keratoconus, corneal scarring, prolate cornea, penetrating keratoplasty, post refractive surgery complication, etc. The aperture is of a sufficient size so as not to be effective as or a substitute for refractive correction.

BACKGROUND OF THE INVENTION

Contact lenses are commonplace today. Most individuals with average refractive errors can quickly and easily acquire and use these lenses in place of prescription eye glasses. For presbyopic individuals, designers have attempted to develop "pinhole" contact lenses. These lenses endeavor to utilize the known theories of pinhole imaging, commonly understood in optics as a method to reduce visual deficiencies. Pinhole mask intraocular lenses also exist for cataract patients (e.g., U.S. Pat. No. 4,955,904 issued to Atebara et al.). A pinhole mask lens conventionally has a clear aperture of up to 4 millimeters in diameter. The annular mask lenses are generally characterized as having a sharp demarcation at the inside and outside edges of the annular mask.

The prior art has focused on the use of "pinhole" contacts for presbyopic individuals (e.g., PCT Publication No. WO 95/08135 published Mar. 23, 1995). However, there is a long felt need for treatment of patients with optical aberration problems, for example, night myopia, which is an increase in refractive error due to the dilation of the pupil and the effect of spherical aberration. Also, increased spherical aberration in patients having radial keratotomy and photorefractive keratectomy due to prolate geometry of the cornea following surgery and aberrations due to corneal distortion and scarring resulting from trauma or genetic conditions including keratoconus. Conventional pinhole contact lens can not adequately address these problems because the loss of retinal illumination due to the pinhole aperture offsets the peripheral distortion benefit.

SUMMARY OF THE INVENTION

The present invention provides, in one aspect, a contact lens with a transparent lens body having an annular mask which gradually increases in transmissivity radially and which defines an aperture whose diameter is of sufficient size so as not to be effective as or a substitute for refractive correction. In other words, the aperture does not provide pinhole effect correction (i.e., refractive substitute correction for myopia, presbyopia, hyperopia, etc.). In a preferred aspect the annular mask reduces or eliminates the effects of night myopia, spherical aberration (i.e., "halos"), aniridia, keratoconus, corneal scaring, penetrating keratoplasty or post refractive surgery complications (among others) by utilizing an annular mask having a "soft" inside edge and that gradually increases the transmissivity radially toward the outer edge of the mask. A lens according to the present invention eliminates or reduces diffraction effects at the inside and outside edges of the annular mask, thereby avoiding a reduction in visual acuity caused by diffraction.

BRIEF DESCRIPTION OF THE DRAWINGS

For a fuller understanding of the nature and objects of the invention, reference should be made to the following detailed description and the accompanying drawings, in which.

DESCRIPTION OF THE PREFERRED EMBODIMENTS

The present invention will now be described with respect to a contact lens, but as will be appreciated by one of ordinary skill in the art, the elements of the present invention include any lens, including but not limited to contact lenses (including rigid or hard lenses, hybrid lenses, hydrogel lenses and gel lenses that do or do not contain water), intraocular lenses, intracorneal lenses, anterior chamber lenses, etc. which are all encompassed by the present invention.

Currently, the tinted pattern on some conventional masked lenses have a clear demarcation between the opaque zone and the partially opaque or transparent zones. Under dim light conditions the iris of the wearer may be dilated to a pupil size greater than the opaque ring. This can create an annular window for forming a "structural halo" which may be visually disturbing. This is believed to be due to the defocused light passing through the annulus of the partially opaque ring or passing around the outer edge of the opaque ring on a conventional masked lens.

Figure 1:
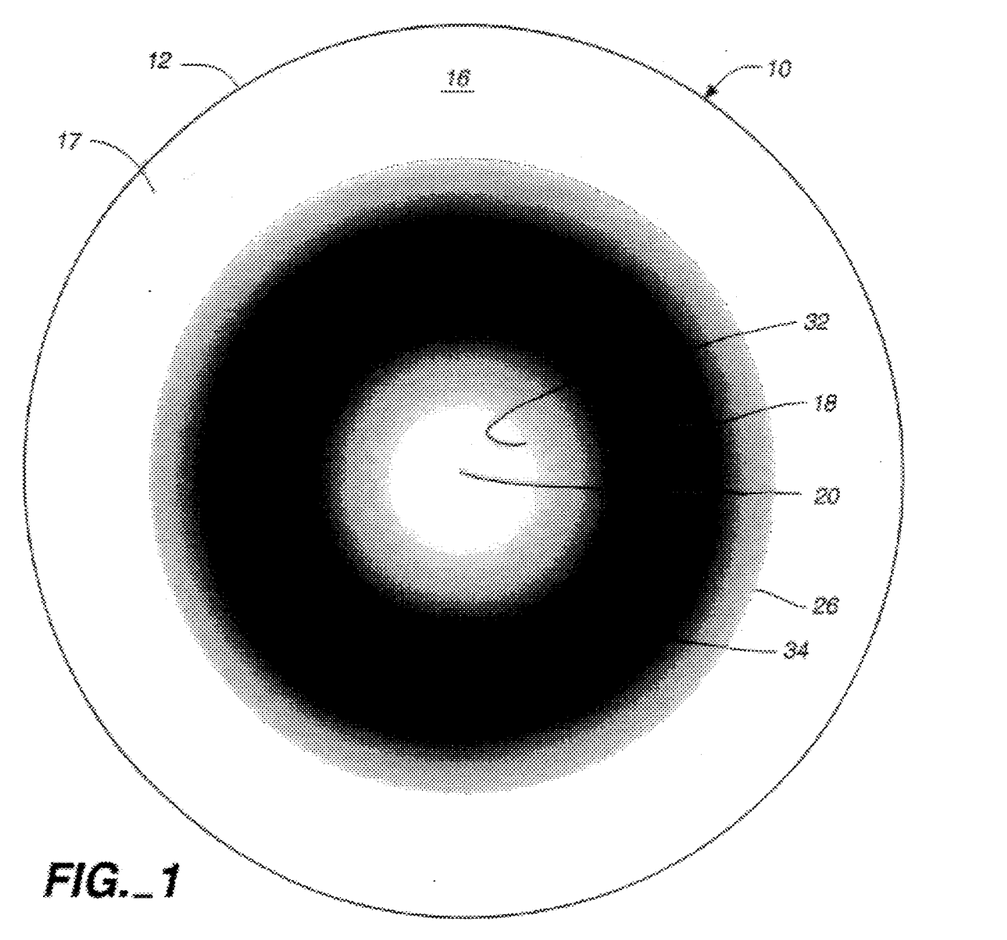
FIG. 1 is a photograph of annular mask in accordance with one embodiment of the present invention with the perimeter of the lens shown by a solid line.

The present invention eliminates the halo by diminishing the distinct demarcation between the opaque and the partially opaque zones or at the outer edge of the opaque ring by radially "tapering" the opacity of the tinted pattern (FIG. 1). In accordance with the present invention, the lens body 12 has a surface configured (e.g., with a concave form) to conform to the eye curvature of the wearer. The lens body 12 has a second surface 16 with a convex form. Optionally, the second surface 16 can be optically configured to correct the vision of the wearer selectively at a focus between and including far and near objects.

The contact lens 10 has an annular mask 18 of continuously variable transmissivity according to the particular needs of a given wearer. The annular mask 18 is arranged to form an aperture 20 at the wearer's optical line-of-sight. The aperture 20 is preferably arranged to be concentric with the wearer's pupil, which could be off-center with respect to the center of the lens body. The aperture 20 is sized to reduce peripheral aberrations and distortions while maximizing retinal illumination. In other words, the aperture is sized to correct optical aberrations with minimal energy starvation to the retina. The aperture is typically of a size greater than conventional "pinhole" contact lenses which produce refractive correction by reducing the retinal blur circle to allow for simultaneous focus of near and distance vision. Therefore, the aperture of the present invention is of sufficient size so as not to be effective as or a substitute for refractive correction. Preferably, the diameter of the aperture is about 3.5 millimeters or larger, more preferably about 4.0 millimeters or larger, more preferably about 4.2 millimeters or larger for individuals having average sized pupils in medium light conditions. The size of the aperture is chosen to be as large as possible for a given wearer while still providing a mask region of sufficient size to treat the conditions described above. However, some individuals have paracentral corneal distortions, therefore, in some instances the aperture diameter may be about 2.0 millimeters or larger, preferably about 3.0 millimeters or larger, (which is within the range of conventional pinhole contact lens) but not be effective as or a substitute for refractive correction, such as for presbyopia.

In one embodiment (FIG. 1), the mask region 18 whether in the form of a coating or other structure, can have various selected levels of transmissivity. Opacity in the annular mask is generally desired for maximum visual sharpness as visual dimness or energy starvation is generally not a problem with the present invention because the aperture diameter is sized so large relative to the wearer's pupil. However, some wearers may want or need more light energy transmitted through the annular mask region 18 to avoid a sense of visual dimness (i.e. to attain more brightness) in medium to low light conditions. For example, the lens 10 (FIG. 1) transmits less light energy towards the central portion 34 of the mask region 18 and transmits relatively more light energy towards the outer edge 26 of the mask region. In one embodiment, the transmissivity transition for the annular mask 18 from less light energy to more light energy utilizes a Gaussian and/or pseudo-Gaussian function to eliminate any sharp demarcation at the edge of the mask region or between the outer edge 26 and any clear region that may exist if the mask region does not extend all the way to the outer region of the lens to avoid the adverse diffraction effects. The transmissivity in the annular mask region can follow any predetermined mathematical function or not be defined by a mathematical function.

In one embodiment, the tapered (progressive) mask pattern has a clear central aperture and the transmissivity of the mask increases gradually from 0% transmissivity at the edge of the clear central aperture to the periphery of the mask. The variation in transmissivity is symmetrical to the axis through the center of the aperture. The aperture 20 typically is greater than the diameter at which diffraction effects start to degrade image quality. In general, the benefits achieved can be destroyed by diffraction if small apertures relative to pupil size are incorporated into the lens. Such small apertures that have these adverse results include radial slits and scalloped patterns. Diffraction can actually increase the blurring of the retina/image such that the wearer's vision is degraded rather than improved. Thus, to maintain retinal illumination and reduce diffraction effects, typically the lower limit of an aperture in a usable contact lens is above about 3.5 millimeters, more preferably above about 4.0 millimeters, more preferably above about 4.2 millimeters.

In one embodiment, the present invention also utilizes a "soft edge" 32 at the junction of the clear aperture 20 and the annular mask 18. This can be accomplished by either reducing the transmittance of the central aperture as a function of increasing radial position, or by decreasing the transmissivity of the annular mask as a function of increasing radial position.

In one embodiment, the present invention eliminates the sharp edge (i.e., abrupt demarcation) by apodizing the aperture. The transmittance function of the aperture 20 on lens 10 (FIG. 1) can be a Gaussian apodized aperture or pseudo-Gaussian apodized aperture described by the function:

$$I(r) = e^{-(r/c)^x}$$

where I(r) is the transmissivity amplitude for the aperture 20 as a function of the radial position, r, and c is the effective radius of the aperture. The effective radius is of sufficient size to reduce peripheral aberrations and distortions but not to be effective as or a substitute for refractive correction. Preferably, the effective radius is in the range from about 2.0 to about 4.2 millimeters, and more preferably in the range from about 3.5 to about 4.0 millimeters, and x is chosen from the range $2 < x \leq 5$. The effective radius is chosen for a particular patient based on the type of optical distortion and the location of that distortion. For example, corneal topography can be utilized to identify the location and severity of keratoconus. Then, c would be chosen based on that location. The function is referred to as Gaussian when x equals 2 and as pseudo-Gaussian for values greater than 2 and preferably no more than 10.

To this point, the aperture apodization as been described as either a Gaussian or pseudo-Gaussian function. However, the present invention is not limited to a Gaussian or a pseudo-Gaussian function to produce the "soft edge" effect. Any number of functions can be used, such as, but not limited to linear, exponential, parabolic, any combination of these, etc. In addition, the present invention is not limited to "soft edges" that are defined by a mathematical function. It is with the scope of the invention that the "soft edge" be defined as any decreasing transmissivity that has diffraction-reducing effect. It is within the scope of the invention that the "soft edge" be defined as any decreasing transmissivity that essentially begins at about 100% and decreases to about 20% or less within a distance in the range of about 0.05 millimeters or greater to about 1.0 millimeters or less, more preferably, decreases to about 10% or less within that distance, more preferably, decreases to about 1% or less within that distance. Likewise, more preferably decreases to about 20% or less within a distance in the range of about 0.1 millimeters or greater to about 1.0 millimeters or less, more preferably decreases to about 10% or less in that distance, more preferably decreases to about 1% or less in that distance. Likewise, more preferably decreases to about 20% or less within a distance in the range of about 0.15 millimeters or greater to about 0.4 millimeters or less, more preferably decreases to about 10% or less in that distance, more preferably decreases to about 1% or less in that distance.

Figure 2:
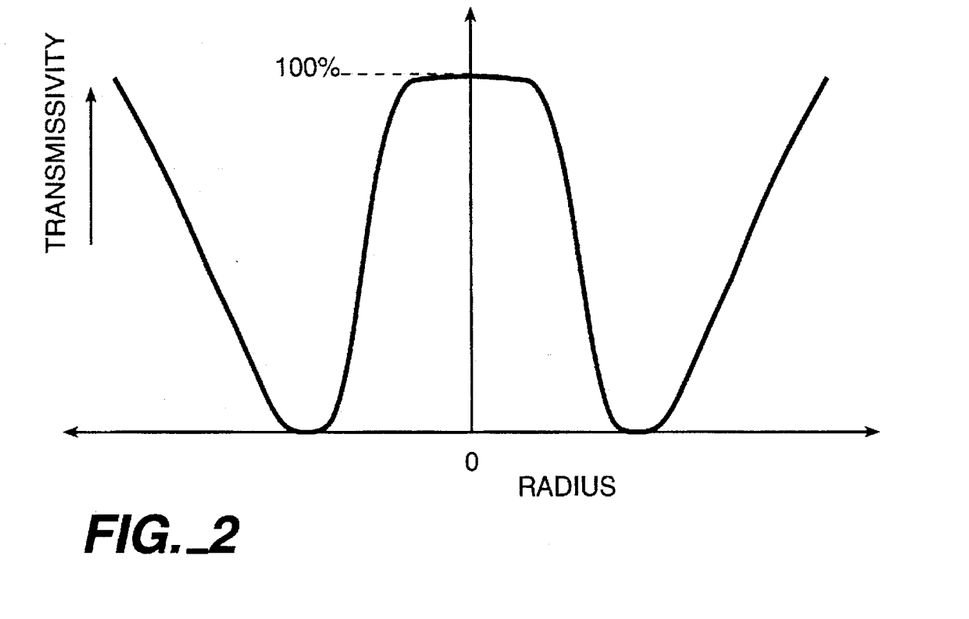
FIG. 2 is a graph of transmittance versus radial position for the annular mask of FIG. 1.

FIG. 2 illustrates the transmissivity for one embodiment of the lens of FIG. 1. The transmissivity at the center of the lens starts at 100% then decreases according to the principles above until reaching a transmissivity below which the mask is opaque or performs as essentially opaque. Preferably, the transmissivity stays at that level for a width of between about 1.0 millimeters to about 4.0 millimeters, preferably about 1.5 to 2.0 millimeters, then increase in transmissivity to the outer "soft edge" 26 or to the edge of the lens. Preferably, the transition in "soft edge" 32 is more rapid than the transition through central portion 34 in the annular mask to its outer portion 26.

An optimal tapering profile of the opaque mask will be related to the pupil sizes and the retinal illumination required for the wearer.

Since the lens may not always center over the wearer's pupil, the lens is preferably fitted first, and the position of the annulus 18 noted, and the lens 10 then made to special order according to the fitting so the annulus 18 centers over the wearer's pupil. Alternatively, the lens can be mass-produced to fit a generalized population of wearers or to fit several sets of generalized wearers. In a preferred embodiment, the lens body 12 is weighted (e.g., with a prism ballast) or shaped to center the aperture 20 at the optimal location on the eye of the wearer, and to reduce the movement of the contact 10 on the wearer's eye, preferably to less than approximately one and one-half millimeters. Accordingly, the lens 10 is held in a relatively constant position on the eye of the wearer, thereby maximizing the lens 10 for central vision while reducing the possibility of a reduction in the peripheral field by decentering and other excessive movements.

In addition, the radial width of the annular mask 18, from the inside edge 32 to the outside edge 26, is preferably between about 0.95 millimeters or greater and about 4.5 millimeters or less. It will be appreciated that the annular mask can extend to the outside edge of the lens and thus its width would be determined by the diameter of the lens. The radial width is sized in the practice of the invention to accommodate the normal function of the human pupil while being effective in treating the above-listed conditions.

The lens body 12 can be constructed with material to form a hard, gas permeable lens, or, alternatively, to form a soft contact lens, e.g., with a flexible soft polymer material. Combinations of these materials are also suitable to form a composite contact. The outer diameter of the contact lens body 12 is approximately seven to eighteen millimeters, depending upon the wearer's eye size. Likewise, the lens body can be constructed with materials suitable for producing anterior chamber lenses, intraocular lenses, intracorneal lenses, etc. It can be appreciated that the dimensions of the annular mask 18 can be adjusted for a particular wearer. For example, the annular mask 18 can be sized for a particular pupil.

Figure 3:
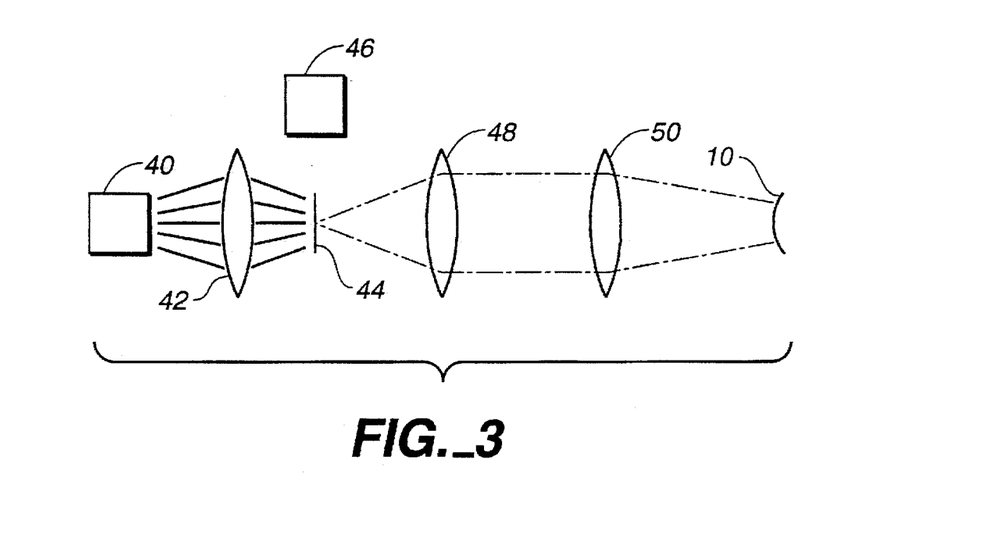
FIG. 3 is a diagrammatic representation of an apparatus used to produce the annular mask of FIG. 1.

Those skilled in the art will appreciate that the mask regions of the lens can be constructed in several ways. In one embodiment, an opaque spinning mask 44 is used to produce an annular mask like the one shown in FIG. 1. The apparatus used with the spinning mask 44 is shown diagrammatically in FIG. 3. The method as described with respect to FIG. 3, can be used to produce a variably transmissive annular mask of any desirable profile depending on the pattern of the spinning mask used. A light source 40 and condenser lens 42 provide back illumination to mask 44 which is spun by motor 46. The spinning mask 44 as an object is imaged through relay lens 48 and imaging lens 50 onto the lens 10 using a photo-reactive dye or coating in or on the lens. The opaque mask has several light transmitting "petals" extending radially outward from a central region. The profile of the variably transmissive annular mask on the resulting lens is controlled by changing the shape of the design of the "petals". As the mask is spinning about an axis symmetric to the petal pattern, the image of the spinning mask becomes an apodized pattern on the lens with continuously variable gray tones.

Figure 4:
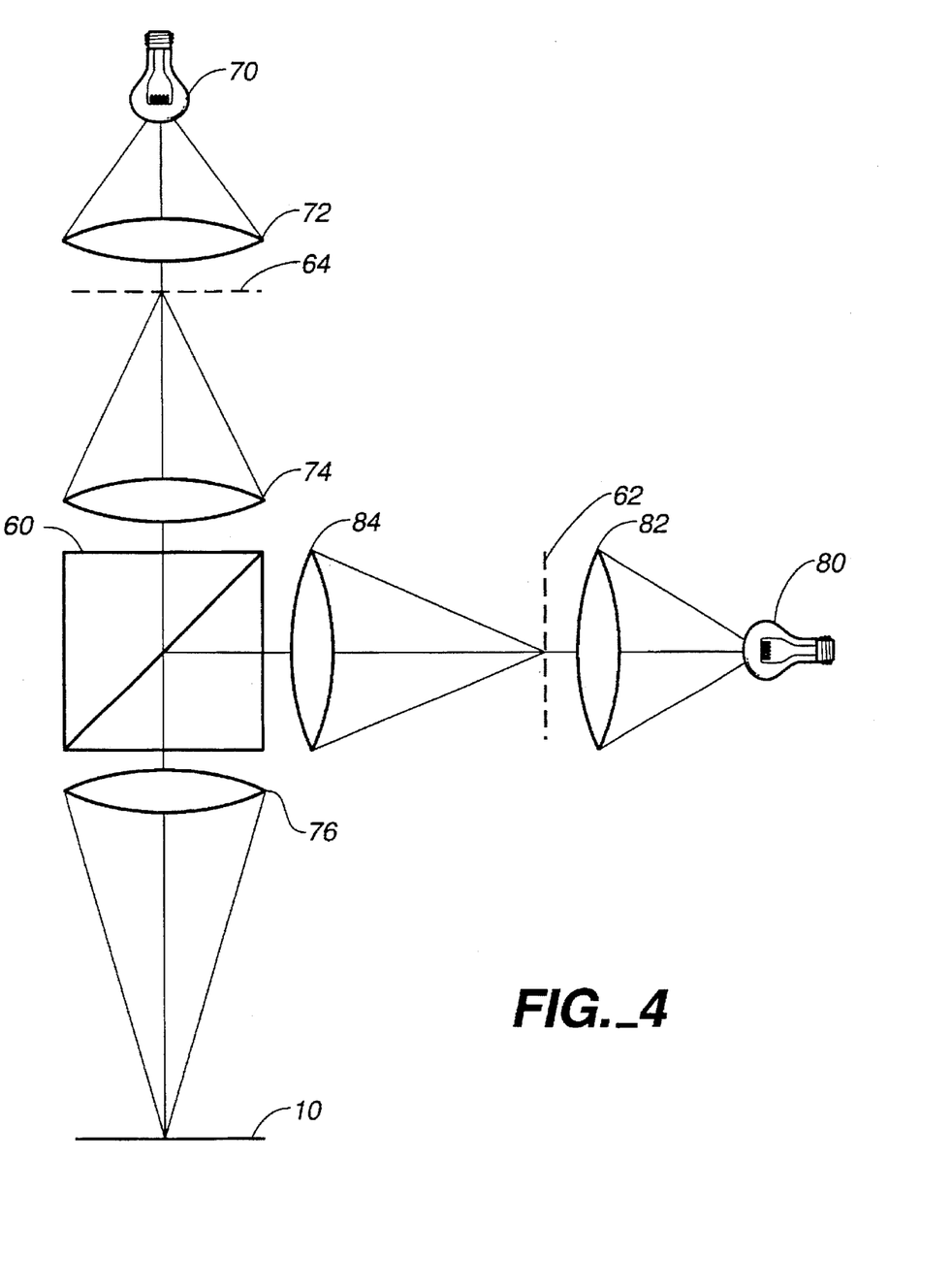
FIG. 4 is a diagrammatic representation of another embodiment of an apparatus used to produce the annular mask of FIG. 1.

Another embodiment, similar to that just described, utilizes a beamsplitter 60 as illustrated diagrammatically in FIG. 4, to combine the apodized aperture pattern with a second spinning mask 62 of any desirable pattern using another projection system branch. In this embodiment, a tapered (i.e., reverse apodized) annular mask pattern is implemented in the second branch of the projection system to produce a masked lens as shown in FIG. 1 having diffraction-reducing edges on the inside of the annular mask and the outside of the annular mask.

Figure 5:
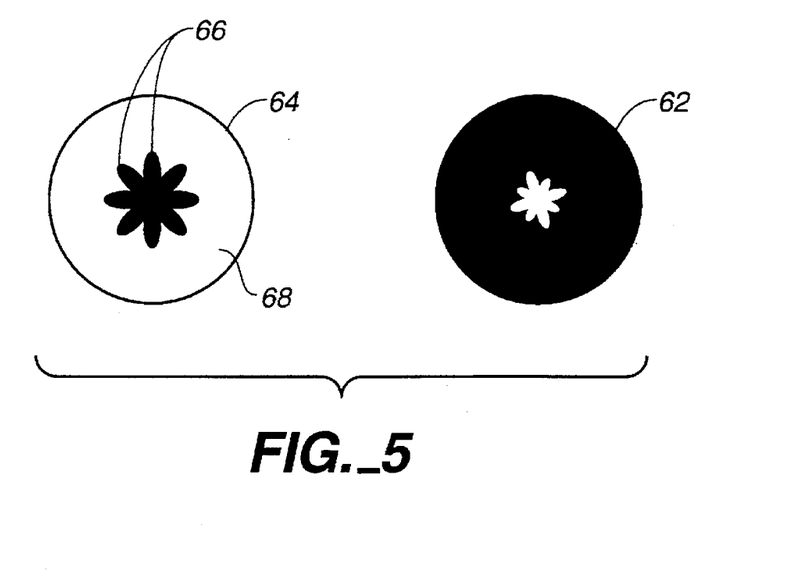
FIG. 5 is a plan view of one embodiment of a set of masks used in the apparatus of FIG. 4.

A mask 64 with a plurality of opaque petals 66 on a light-transmitting substrate disk 68 (FIG. 5) is illuminated by a light source 70 and condenser lens 72 (FIG. 4). A magnified or demagnified image of the mask 64 is formed on the lens 10 by relay and imaging lenses 74, 76. As the mask 64 is spinning about an axis symmetric to the blade pattern, the image of the spinning mask becomes a brightness-tapered pattern with continuous gray tones. The brightness tapered profile of the image is controlled by the design of the shape of the petals. A second mask 62 of any desirable pattern, such as shown in FIG. 5, is illuminated by a second light source 80 and condenser lens 82. A second magnified or demagnified image is formed on the lens 10 by relay and imaging lenses 84, 76 and beamsplitter 60. The final image is a combined image of the individual images superimposed on the lens 10. By controlling the brightness of the light sources and/or exposure time for each mask, a combined image of any desired transmissivity pattern can be produced in the lens.

Figure 6:
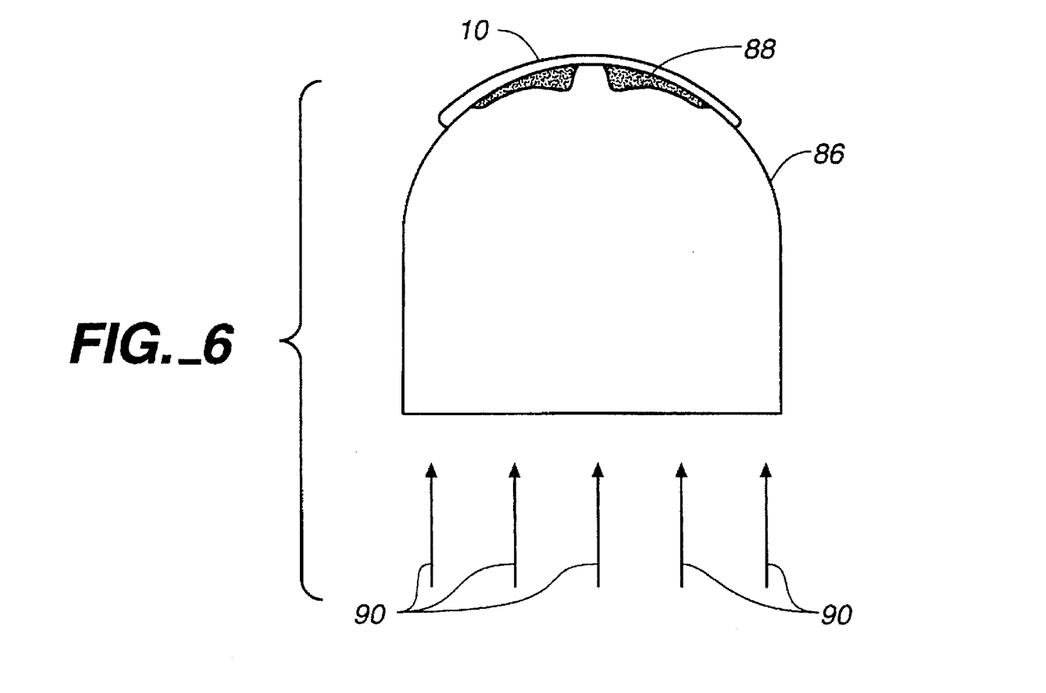
FIG. 6 is an apparatus for use in another method for producing the present invention.

In another embodiment, a transparent dome 86 (FIG. 6) having a light-occluding portion 88 is used to produce the annular mask pattern in the lens. The dome 86 has a groove machined into the top of the dome beginning at a depth of about 0.1 millimeters deep in the region surrounding an area not machined out that will form the central aperture on the lens and rapidly increasing to a depth of about 1.0 millimeters at a diameter of about 3.5 millimeters then gradually decreasing to a depth of 0.1 millimeters at an outside diameter of 5.5 millimeters. The groove is filled with black blocking wax to form light occluding portion 88. In use, the lens 10 is emersed in a Diazo dye solution (HD-61; see full chemical name in Example 1) and then placed on the dome 86 in position so that the light-occluding portion of the dome is in the position where the resulting annular mask should be on the finished lens. Light 90 is shone from beneath the dome until all exposed areas of the lens become discolored. A typical light source is a HA 6000 halogen ELH or ENX lamp. The lens is then placed into phloroglucinol solution in which the areas of the lens corresponding to the light-occluding part of the dome turn black and form a continually variable shade of gray resulting in an annular mask pattern such as shown in FIG. 1.

Figure 7:
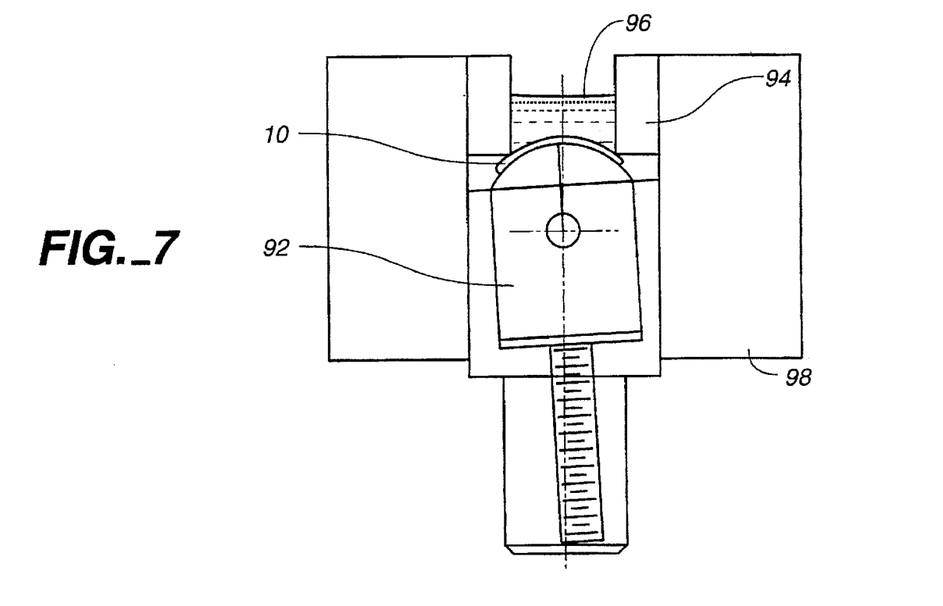
FIGS. 7 and 8 illustrate a further embodiment for producing the present invention.
Figure 8:
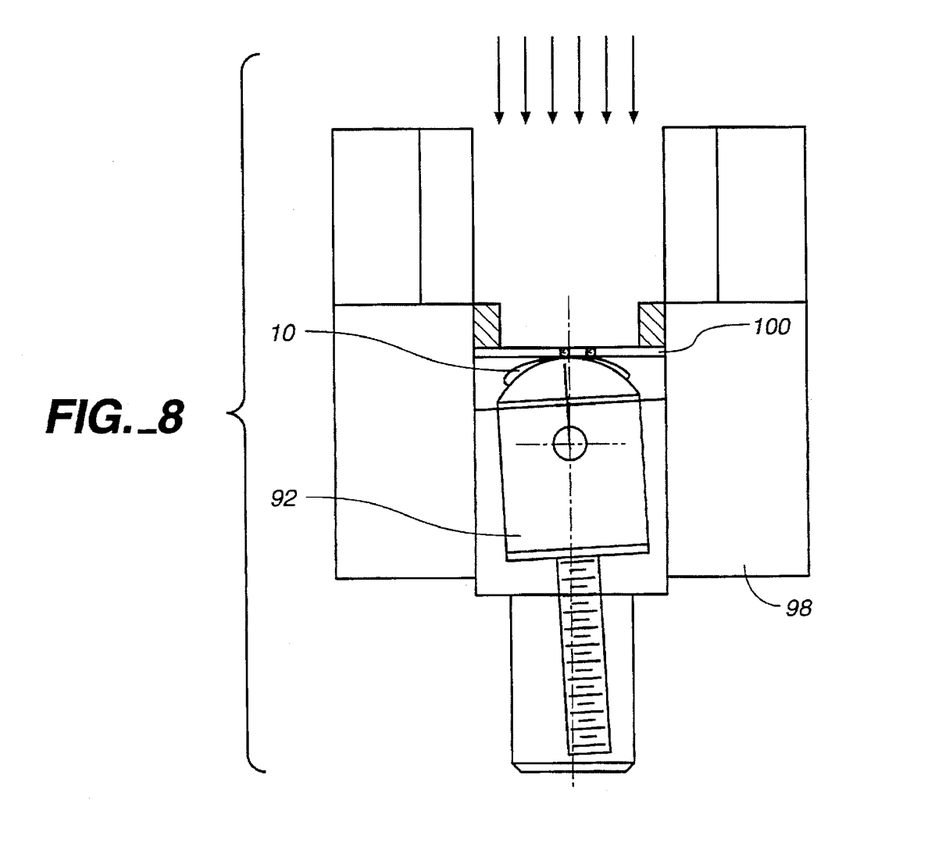

In another embodiment, the lens 10 is positioned correctly on an opaque dome 92 in housing 98, and then contacted with a dam ring 94 to hold dye solution 96 (FIG. 7). Dye solution is placed in the dam ring and allowed to permeate the lens from the top side of the lens only. Dye is allowed to diffuse into the lens only to a depth necessary to produce the desired intensity, and not all the way through the thinnest section of the lens. After the dye has penetrated the lens 10, the dam ring is removed and the dye rinsed off the surface quickly with water. A light restricting mask 100 is then placed over the lens 10 and the dye in the lens is desensitized by exposure to light (FIG. 8). The mask 100 is produced on a computer monitor with a commercially available graphics program. Then either printed out on clear film or a slide is made with a 35 millimeter camera of the computer-generated mask pattern. The slide film is then used as the mask 100. Alternatively, the mask 100 can be produced by methods such as but not limited to selection of appropriate neutral density or color filters, metal deposition, such as sputtering, vacuum deposition, printing, spraying, etc.

In order to achieve a more graduated or tapered edge, the mask can be raised slightly above the lens, so that a diffused edge will form from light diffraction effects. By varying the distance of the mask from the lens, the light intensity, duration of exposure to the light, and quality of light in the lens, different tapering effects may be produced in the lens.

Another practice uses a variably transmissive coating applied to, or manufactured with, the lens body. Yet another practice generates the annular mask with a plurality of light-blocking dots, which in total reduce the transmission of light energy through the annulus to the selected transmissivity. Another practice uses a shutter-like mechanical device (not shown) with several shutter blades arranged to provide masking in three concentric annular regions corresponding to the inner soft edge, the opaque portion and the outer soft edge. The opaque region will be fixed with 1% transmissivity or less. The transmissivity of the inner soft edge and the outer soft edge can be varied with the speed of the shutter blades opening and closing and with the shape of the shutter blades.

Other practices for forming the annular mask include other Diazo contact printing processes, mesoprints, and reactive and vat dyes. Other practices for forming the annular mask include a variety of methods for disrupting the surface or refractive properties of the lens in the area of the annular mask. For example, lasers or chemical etchants, or physical abrasives, are effectively used to disrupt the optical surface of the contact to change the transmission in the annular mask region to form the annular mask. Suitable techniques for disrupting and creating such optical surfaces are described in U.S. Pat. No. 4,744,647, entitled "Semi-Opaque Corneal Contact Lens or Intraocular Lens and Method of Formation".

Another embodiment for achieving the variably transmissive annular mask utilizes PAD FLEX™ or Italio Plate methodology, which is well-known to those skilled in the art. In PAD FLEX™ printing, for example, a silicone tip contacts an Italio plate engraved with a selectable pattern and filled with ink. The tip acquires the image from the Italio plate and then transfers the image without distortion onto a wide range of curved surfaces, such as a contact lens.

In another method of imparting the annular mask to the contact lens, the mask comprises a pigment suspended in a solvent material which is applied to the surface of a contact lens mold, and the contact lens is cast and polymerized thereabouts. This means that the mask is incorporated into the body of the lens as part of the contact lens surface or into the lens body in the region immediately adjacent to the lens surface.

Suitable pigments for use with this method include:

| Color Index | Chemical Name |
| --- | --- |
| Pigment Black 7 | Carbon Black |
| Pigment Black 11 | Iron Oxide |
| Pigment Brown 6 | Iron Oxide |
| Pigment Red 101 | Iron Oxide |
| Pigment Yellow 42 | Iron Oxide |
| Pigment White #6 | Titanium Oxide |
| Pigment Green #17 | Chromic Oxide |
| Pigment Blue #36 | Chromium-Aluminum-Cobaltous Oxide |
| Pigment Green #7 | Poly chloro copper phthalocyanine |
| Pigment Blue #15 | Copper phthalocyanine |
| Pigment Violet #23 | 3, amino-9-ethyl carbazole-chloranil |

Furthermore, the above mentioned pigments may be mixed with one another to produce the desired variably transmissive mask. Likewise, precipitated vat dyes, including precipitated version of those disclosed earlier may be used as suitable pigments in the above method.

In another embodiment for incorporating the variably transmissive mask into the body of the lens, pigment is dispersed in a polymerisable medium which is then applied to the surface of a contact lens casting mold and the contact lens is cast and polymerized thereabouts. In this particular instance as the main body of the lens is polymerized so is the polymerisable medium in which pigment is incorporated into the contact lens as part of the surface of the contact lens or immediately adjacent thereto.

The pigments which may be used with this particular arrangement of the present invention include those disclosed above for use with the earlier disclosed methods, which may be dispersed in the same monomeric materials as that from which the contact lens is formed.

In another embodiment, a rod of polymeric material is formed, which rod has a band of variably transmissive material throughout its length, this rod is then cut into buttons from which the contact lenses are then machined. In its simplest form this method may be used to produce individual buttons and not a rod.

A contact lens constructed in accordance with the invention is colored, tinted, or otherwise shaded, when appropriate, by methods known in the art. This coloring or tinting can be cosmetic, as it often is for many wearers of common contact lenses. It can also reduce the sometimes objectionable appearance of the annular mask 18 when viewed on the eye of the wearer. For example, the invention provides for an annulus that is matched to the wearer's iris. It also provides for an annulus that enhances or changes the appearance of the wearer's iris, if desired. A further enhancement can include a limbal ring as described in U.S. Pat. No. 5,302,978 which is incorporated herein by reference in its entirety.

It will be understood that changes may be made in the above constructions without departing from the scope of the invention. For example, the arrangement and size of the annular mask 18, can be selected for a particular wearer to optimize the visual correction available. In another example, the contact lens body 12 can be constructed with a yellow appearance, giving the wearer a physiological impression of brighter lighting. Those skilled in the art will appreciate that the invention can also aid wearers suffering from other vision deficiencies and disorders.

EXAMPLE 1

A contact lens in accordance with FIG. 1 was produced with the following procedure. A 1% sensitizer solution was formed by dissolving 1.0 grams of 4-diazo-[4'-toluyl]-mercapto-2,5-diethoxybenzene zinc chloride (also referred to as Diazo-15 or HD-61) in 100.0 grams of de-ionized water and sonicating for 15 to 20 minutes. A 1% developer solution was formed by dissolving 1.0 grams of phloroglucinol dihydrate in 100.0 grams of de-ionized water and sonicating for 15–20 minutes. The solutions were filtered using 0.45 micron filter paper prior to use. Prior to tinting, the lens was equilibrated in water for at least 1 hour. The lens was then pat dry and dropped in a vial containing about 6–8 milliliters of sensitizer. The front curve of the lens was uppermost. The lens was left in the solution for 3 minutes. The lens was removed, rinsed with water and pat dry. The lens was positioned on a dome and the imaging mask pattern placed over the lens on the dome. The dome was then placed over a type ENX HA 6000 Halogen light source for 2 minutes. The lens was then removed from the dome and placed in the developer solution for 2 minutes. The lens was then rinsed with clean water and processed via the usual extraction and hydration processes.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A lens adapted to be worn on or implanted in the eye for correcting optical aberrations, comprising:

an aperture having a diameter of sufficient size so as not to be effective as or a substitute for refractive correction; and an annular mask region surrounding the aperture wherein the annular mask region transmits less light energy than the aperture in a portion adjacent to an outer region of the aperture and more light energy towards an outer edge of the annular mask region than the portion adjacent to the outer region of the aperture without demarcation in the change in transmissivity within the annular mask region.

2. The lens of claim 1 wherein the aperture is of selected transmissivity such that the aperture transmits more light energy than the annular mask region at a center of the aperture and less light energy toward the outer region of the aperture than the center of the aperture.

3. The lens of claim 1 wherein the transmissivity of the annular mask region varies as a predetermined mathematical function of the distance from the center of the aperture.

4. The lens of claim 3 wherein the mathematical function is a Gaussian distribution.

5. The lens of claim 3 wherein the mathematical function is given by the equation, $$\text{transmissivity amplitude} = e^{-(r/c)^x}$$

where r=radial position in millimeters c=effective radius of the aperture in millimeters x=a constant in the range of about 2 to about 10.

6. The lens of claim 1 wherein the annular mask region adjacent to the outer region of the aperture has a transmissivity below which the annular mask region functions as essentially opaque, remains at that amount of transmissivity or less for a distance in the range of about 0.5 millimeters to about 4.0 millimeters in a radial direction, then increases in transmissivity until reaching an outer edge of the annular mask region or the lens.

7. The lens of claim 1 wherein the annular mask region adjacent to the outer region of the aperture has a transmissivity below which the annular mask region functions as essentially opaque, remains at that amount of transmissivity or less for a distance in the range of about 1.5 millimeters to about 2.0 millimeters in a radial direction, then increases in transmissivity until reaching an outer edge of the annular mask region or the lens.

8. The lens of claim 2 wherein the transmissivity of the aperture varies as a predetermined mathematical function of the distance from the center of the aperture.

9. The lens of claim 8 wherein the mathematical function is a Gaussian distribution.

10. The lens of claim 8 wherein the mathematical function is given by the equation, $$\text{transmissivity amplitude} = e^{-r/c^x}$$

where r=radial position in millimeters c=effective radius of the aperture in millimeters x=a constant in the range of about 2 to about 10.

11. The lens of claim 8 wherein the mathematical function is given by the equation, $$\text{transmissivity amplitude} = e^{-(r/c)^x}$$

where r=radial position in millimeters c=effective radius of the aperture in millimeters x=a constant in the range of about 2 to about 5.

12. The lens of claim 11 wherein c is selected from the range of about 2.0 to about 4.2 millimeters.

13. The lens of claim 11 wherein c is selected from the range of about 3.5 millimeters to about 4.0 millimeters.

14. The lens of claim 1 wherein the lens is a contact lens.

15. The lens of claim 1 wherein the lens is an intraocular lens.

16. A lens adapted to be worn on or implanted in the eye for correcting optical aberrations, comprising:

a clear aperture having a diameter of sufficient size so as not to be effective as or a substitute for refractive correction; and an annular mask region having a transmissivity in which the annular mask region transmits less light energy toward the clear aperture than the clear aperture and more light energy toward an outer portion of the annular mask region than the less light energy portion without a demarcation in the change in transmissivity within the annular mask region.

17. The lens of claim 16 further comprising:

an annular portion adjacent to the clear aperture having a transmissivity in which the annular portion transmits more light energy at an inner region than the annular mask and less light energy toward an outer region adjacent to the annular mask than the inner region of the annular portion.

18. The lens of claim 16 wherein the diameter of the clear aperture is about 3.5 millimeters or greater.

19. The lens of claim 16 wherein the diameter of the clear aperture is about 4.0 millimeters or greater.

20. The lens of claim 16 wherein the diameter of the clear aperture is about 4.2 millimeters or greater.

21. The lens of claim 16 wherein the transmissivity of the annular mask region varies as a predetermined mathematical function of the distance from the center of the clear aperture.

22. The lens of claim 21 wherein the mathematical function is a Gaussian distribution.

23. The lens of claim 21 wherein the mathematical function is given by the equation, $$\text{transmissivity amplitude} = c^{-(r/c)^x}$$

where r=radial position in millimeters c=effective radius of the aperture in millimeters x=a constant in the range of about 2 to about 10.

24. The lens of claim 17 wherein the annular portion decreases from about 100% transmissivity to a transmissivity below which the annular mask region functions as essentially opaque, remains at that mount of transmissivity or less for a distance in the range of about 1.0 millimeters to about 4.0 millimeters in the radial direction, then increases in transmissivity until reaching an outer edge of the annular mask region or the lens.

25. The lens of claim 17 wherein the annular portion decreases from about 100% transmissivity to a transmissivity below which the annular mask region functions as essentially opaque, remains at that amount of transmissivity or less for a distance in the range of about 1.5 millimeters to about 2.0 millimeters in the radial direction, then increases in transmissivity until reaching an outer edge of the annular mask region or the lens.

26. The lens of claim 17 wherein the annular portion decreases from about 100% transmissivity to about 20% transmissivity in a distance in the range of about 0.05 millimeters to about 1.0 millimeters in the radial direction.

27. The lens of claim 17 wherein the annular portion decreases from about 100% transmissivity to about 20% transmissivity in a distance in the range of about 0.15 millimeters to about 0.4 millimeters in the radial direction.

28. The lens of claim 17 wherein the annular portion decreases from about 100% transmissivity to about 10% transmissivity in a distance in the range of about 0.05 millimeters to about 1.0 millimeters in the radial direction.

29. The lens of claim 17 wherein the annular portion decreases from about 100% transmissivity to about 10% transmissivity in a distance in the range of about 0.15 millimeters to about 0.4 millimeters in the radial direction.

30. The lens of claim 17 wherein the annular portion decreases from about 100% transmissivity to about 1% transmissivity in a distance in the range of about 0.05 millimeters to about 1.0 millimeters in the radial direction.

31. The lens of claim 17 wherein the annular portion decreases from about 100% transmissivity to about 1% transmissivity in a distance in the range of about 0.15 millimeters to about 0.4 millimeters in the radial direction.

32. A method for treating optical aberrations of a patient's eye, comprising:

fitting the patient with a lens;

applying to the lens an annular mask region having an aperture having a diameter of sufficient size so as not to be effective as or a substitute for refractive correction wherein the annular mask region transmits less light energy than the aperture in a portion adjacent to the aperture and more light energy towards an outer edge of the annular mask region than the portion adjacent to the aperture without a demarcation in the change in transmissivity within the annular mask region; and placing the lens on the patient's eye.

* * * * *